United States Patent [19]

(12) United States Patent
Cruse et al.

(10) Patent No.: US 8,829,257 B2
(45) Date of Patent: Sep. 9, 2014

(54) TRIVINYLCYCLOHEXANE STEREOISOMERIC COMPOSITIONS AND METHODS FOR PREPARING SAME

(75) Inventors: Richard W. Cruse, Yorktown Heights, NY (US); Vivek Khare, Bangalore (IN); Jozef Kowalski, Lodz (PL); Wlodzimierz Stanczyk, Lodz (PL)

(73) Assignee: Momentive Performance Materials Inc., Waterford, NY (US)

( * ) Notice: Subject to any disclaimer, the term of this patent is extended or adjusted under 35 U.S.C. 154(b) by 180 days.

(21) Appl. No.: 13/547,703

(22) Filed: Jul. 12, 2012

(65) Prior Publication Data

US 2013/0018212 A1    Jan. 17, 2013

Related U.S. Application Data

(60) Provisional application No. 61/508,336, filed on Jul. 15, 2011.

(51) Int. Cl.
C07C 5/29       (2006.01)
C07C 13/19      (2006.01)
C07C 5/22       (2006.01)

(52) U.S. Cl.
CPC ............... *C07C 5/22* (2013.01); *C07B 2200/07* (2013.01); *C07C 5/29* (2013.01); *C07C 2101/14* (2013.01)
USPC ............. 585/20; 585/350; 585/371; 585/372; 585/373; 585/374

(58) Field of Classification Search
CPC .......... C07C 13/19; C07C 13/18; C07C 5/29; C07C 5/27
USPC .................... 585/20, 371, 350, 372, 373, 374
See application file for complete search history.

(56) References Cited

U.S. PATENT DOCUMENTS

| | | | | |
|---|---|---|---|---|
| 2,967,895 A * | 1/1961 | Derichs et al. | | 585/20 |
| 3,011,003 A * | 11/1961 | Wilke et al. | | 585/20 |
| 3,227,780 A * | 1/1966 | Brack | | 525/14 |
| 7,045,488 B2 * | 5/2006 | Bartley et al. | | 508/110 |
| 7,488,859 B2 * | 2/2009 | Huang et al. | | 585/352 |
| 7,674,861 B1 | 3/2010 | York et al. | | |
| 8,026,402 B2 * | 9/2011 | Hassan et al. | | 585/270 |
| 2003/0176313 A1* | 9/2003 | Ellwood et al. | | 512/8 |
| 2010/0112258 A1 | 5/2010 | Cruse et al. | | |
| 2010/0113681 A1 | 5/2010 | O'Brien | | |

FOREIGN PATENT DOCUMENTS

GB    848637    6/1960
SU    390058    7/1973

OTHER PUBLICATIONS

Attridge et al., J. Chem. Soc. C., (1971) 2999-3001.
Maas et al., Tetrahedron Letters, 24(21) (1983) 2143-2146.
G. Wilke, Angewandte Chemie, 75: (1963) 105-115.

* cited by examiner

*Primary Examiner* — Ellen McAvoy
(74) *Attorney, Agent, or Firm* — Dominick G. Vicari; Joseph S. Ostroff

(57) ABSTRACT

Disclosed herein is a process for making 1,2,4-trivinylcyclohexane that is enriched in a particular geometric isomer. The process involves the thermal isomerization of 1,5,9-cyclododecatriene at temperature between 400° C. and 600° C. followed by an equilibration of the resultant intermediate in either the gas phase or liquid phase at temperature between 180° C. and 375° C. and at pressures ranging from 0.101 kPa to 1,013 kPa. Also disclosed are 1,2,4-trivinylcyclohexane compositions that are enriched in a particular geometric isomer.

21 Claims, 4 Drawing Sheets

Equilibration step provided via a heated pipe downstream of the hot tube reactor

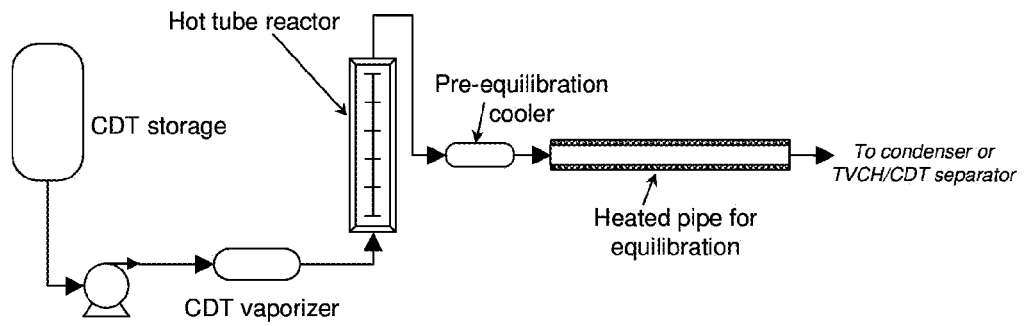
Figure 1 Equilibration step provided via a heated pipe downstream of the hot tube reactor
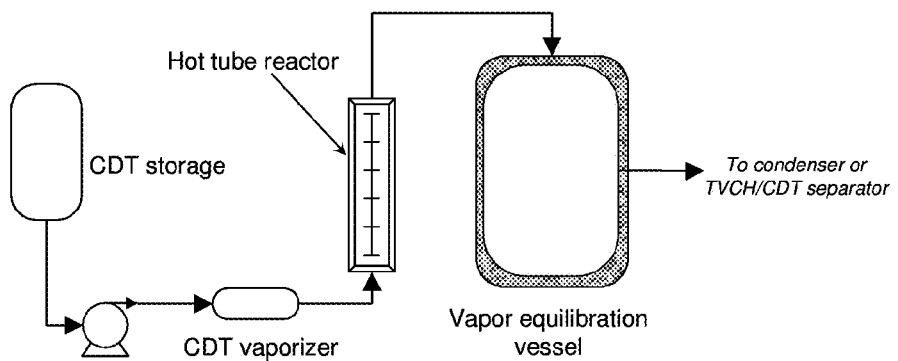
Figure 2 Equilibration step provided via a suitably sized Vapor Equilibration Vessel maintained at the equilibration temprature

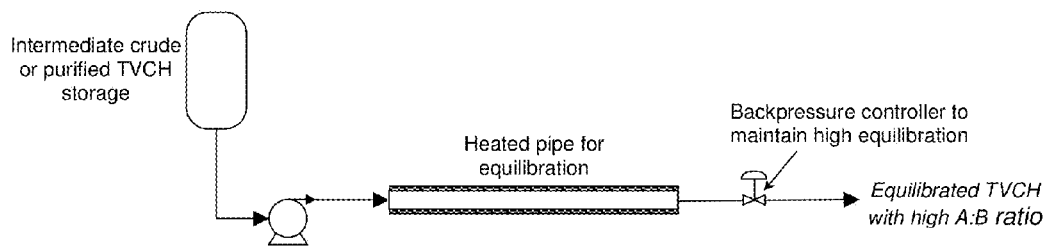
Figure 3 Continuous arrangement for conducting liquid phase
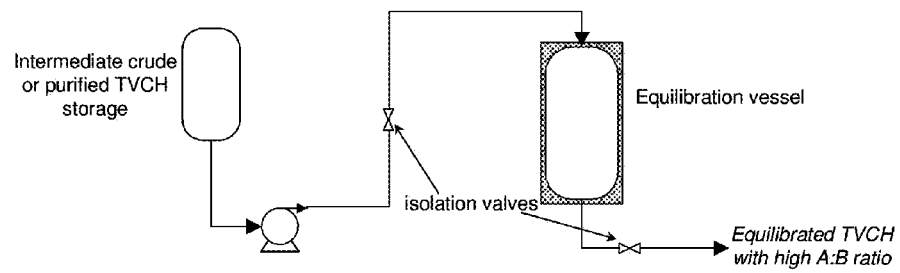
Figure 4 Semi-batch arrangement for conducting liquid phase equilibration

TRIVINYLCYCLOHEXANE STEREOISOMERIC COMPOSITIONS AND METHODS FOR PREPARING SAME

CROSS REFERENCE TO RELATED APPLICATIONS

This application claims the benefit of U.S. Provisional Application Ser. No. 61/508,336 filed Jul. 15, 2011, the disclosure of which is incorporated herein by reference in its entirety.

FIELD OF INVENTION

The present invention relates to trivinylcyclohexane stereoisomeric compositions containing enriched levels of Isomer A and methods for preparing same.

BACKGROUND OF THE INVENTION

Trivinylcyclohexanes are known and can be prepared by the thermal rearrangement of 1,5,9-cyclododecatriene (CDT). Wilke and coworkers in U.S. Pat. No. 3,011,003 and in Angew. Chem., 75 (1963) 27 disclose such a process, which comprises (1) heating CDT in the absence of a catalyst to a temperature between 300° C. and 650° C. thereby forming trivinylcyclohexane product, and (2) separating out the trivinylcyclohexane product by distillation. Although a broad reaction temperature range has been disclosed, according to the patentees, particularly suitable reaction temperatures are between 450° C. and 550° C. The reason is that the rearrangement proceeds considerably more slowly at lower temperatures and other lower molecular weight hydrocarbons, including butadiene, are formed at higher temperatures.

Trivinylcyclohexanes can also be prepared in the presence of a catalyst, typically a metal or a metal oxide. Examples of the catalysts are palladium, chromium oxide, iron oxides, and a wide range of mixed transition and/or main group metal oxides. Illustratively, U.S. Pat. No. 2,967,895 and GB 848637 disclose a process, which includes heating CDT at temperatures between 400° C. and 600° C. in the presence of a palladium catalyst. According to the patentees, no reaction takes place at lower temperatures and troublesome side reactions predominate at higher temperatures. Chromium oxide ($Cr_2O_3$), which contains smaller quantities of $K_2O$, $CaO$, $NiO$ and $P_2O_5$, on an $Al_2O_3$ support, has also been disclosed as a catalyst for preparing 1,2,4-trivinylcyclohexane, as for example, in SU 390058. The temperatures utilized in this process are from 350° C. to 500° C.

Unfortunately, these prior art processes typically have low selectivity and poor conversion rates and result in mixture of several stereoisomers. None of the prior art references disclose or suggest distinction among isomers, much less any processes to provide trivinylcyclohexane enriched in any particular isomer.

Accordingly, there is a need for a commercial and cost-effective process to produce 1,2,4-trivinylcyclohexane that is enriched in a desirable isomer and can be made in high yields and with high selectivity. The present invention provides an answer to that need.

SUMMARY OF THE INVENTION

In one aspect, the present invention relates to a process for preparing a 1,2,4-trivinylcyclohexane composition enriched in Isomer A, the lowest boiling geometric isomer of 1,2,4-trivinylcyclohexane, comprising: (i) heating 1,5,9-cyclododecatriene at a temperature of from about 400° C. to about 600° C. and at a pressure of from about 1 mbar to about 1.2 bar thereby forming a 1,2,4-trivinylcyclohexane composition containing low levels of Isomer A; and (ii) equilibrating the composition from step (i) in a vapor phase or a liquid phase at a temperature ranging from about 180° C. to about 375° C. and at a pressure ranging from about 1 mbar to about 10 bar to produce a 1,2,4-trivinylcyclohexane composition enriched in Isomer A as compared to the composition of step (i).

In another aspect, the present invention is directed to a process for preparing 1,2,4-trivinylcyclohexane compositions enriched in Isomer A comprising: equilibrating a 1,2,4-trivinylcyclohexane composition containing low levels of Isomer A in a vapor phase or a liquid phase at a temperature ranging from about 180° C. to about 375° C. and at a pressure ranging from about 1 mbar to about 10 bar to produce a 1,2,4-trivinylcyclohexane composition enriched in Isomer A.

In another aspect, the present invention relates to a 1,2,4-trivinylcyclohexane composition enriched in Isomer A, wherein the molar ratio of Isomer A to Isomer B is from 4:1 to 99.9:1, advantageously from 4:1 to 10:1. These compositions can be prepared from the careful fractional distillation of the equilibrated products prepared from the processes of the present invention.

These and other aspects will become apparent upon reading the detailed description of the invention.

BRIEF DESCRIPTION OF THE DRAWINGS

FIG. 1 illustrates an equilibration step provided via a heated pipe downstream of a hot tube reactor.

FIG. 2 illustrates an equilibration step provided via a suitably sized vapor equilibration vessel maintained at the equilibration temperature.

FIG. 3 illustrates a continuous arrangement for conducting liquid phase equilibration.

FIG. 4 illustrates a semi-batch arrangement for conducting liquid phase equilibration.

Figure 5:
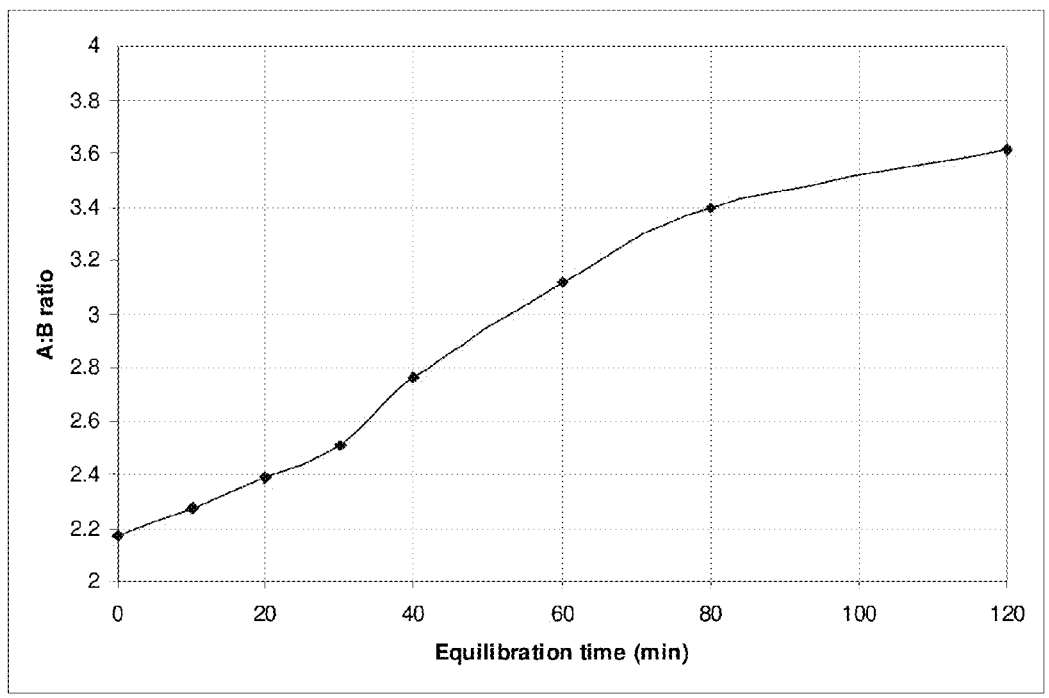
FIG. 5 illustrates the effect of equilibration time on Isomer A enrichment.

DETAILED DESCRIPTION OF THE INVENTION 1,2,4-tricyclohexane (TVCH) has four geometric stereoisomers. These four geometric stereoisomers are referred to herein as Isomer A, Isomer B, Isomer C, and Isomer D. Their designations as A, B, C, or D are based on the order in which they are collected when distilled through a fractionating column, A being the first, and D the last. The order was determined experimentally through a careful fractional distillation using a 38.1 mm inner diameter and 122 cm length, silvered vacuum jacketed column packed with 316 stainless steel protruded packaging (3/16 inch size) available from H.S. Martin, Inc. The following temperatures were measured with a type K thermocouple. The fractional separation of Isomer A occurred at 45° C. and a pressure 0.133 kPa (1 ton). Isomer B was separated at 0.6° C. higher temperature than Isomer A. Isomer C was separated at 1° C. higher in temperature than Isomer B. Isomer D was separated at 0.5° C. higher temperature than Isomer C. The inventors believe that the structures of Isomer A, Isomer B and Isomer C, and Isomer D correspond to structures shown in Table 1.

TABLE 1

Stereoisomers of 1,2,4-trivinylcyclohexane

| Name of isomer | Two-dimensional structure | Three-dimensional structure |
|---|---|---|
| 1,trans-2,trans-4-trivinyl-cyclohexane Isomer A | | |
| 1,trans-2,cis-4-trivinyl-cyclohexane Isomer B | | |
| 1,cis-2,trans-4-trivinyl-cyclohexane Isomer C | | |
| 1,cis-2,cis-4-trivinyl-cyclohexane Isomer D | | |

The analysis of the Isomer ratios was determined by Gas Chromatography (GC), using the following equipment and conditions:
GC Type: HP 6890 Series Gas Chromatograph, Capillary S/Si inlet, Flame Ionization Detector;
Gas: Air at 60 psi; He at 50 psi; and $H_2$ at 30 psi;
Column Type: Restek Rtx®-65 Columns (fused silica) (mid to high polarity phase; Crossbond® 65% diphenyl/35% dimethyl polysiloxane)
Column Length: 30 meters
Internal Diameter: 0.25 mm
df 0.25 µm

| Oven Ramp: | degrees C./min. | Next degrees C. | Hold minutes |
|---|---|---|---|
| Initial | | 80 | 2 |
| Ramp 1 | 10 | 200 | 1 |

Total run time = 15 minutes.

Through the inventors' experiments, it was observed that isomer A can be more efficiently hydrosilated as compared to isomer B under the same reaction conditions. Hydrosilation product of 1,2,4-trivinylcyclohexane is a valuable compound for various applications. For example, it can be used as a key intermediate in the synthesis of sulfur silanes used to impart low rolling resistance to automobile tires.

In addition, under certain circumstances, such as for example, the production of silane coupling agents for use in filler reinforced elastomers, compositions containing trivinylcyclohexane enriched in Isomer A are desirable as intermediates to produce compositions that have high coupling efficiency.

Unfortunately, it was observed by the inventors that the 1,2,4-trivinylcyclohexane compositions prepared by the conventional processes typically contain mixtures of stereoisomers having low levels of Isomer A, for example having a molar ratio of Isomer A to Isomer B less than 2.2:1.

It has now been surprisingly found that 1,2,4-trivinylcyclohexane composition enriched in Isomer A can be prepared by the processes of the invention.

In one embodiment, the process of the invention comprises the steps of:

(i) heating 1,5,9-cyclododecatriene at a temperature of from about 400° C. to about 600° C. and at a pressure of from about 0.101 kPa to about 121.5 kPa thereby forming a 1,2,4-trivinylcyclohexane composition containing low levels of Isomer A;

(ii) equilibrating the composition from step (i) in a vapor phase or a liquid phase at a temperature ranging from about 180° C. to about 375° C. and at a pressure ranging from about 0.101 kPa to about 1,013 kPa to produce a 1,2,4-trivinylcyclohexane composition enriched in Isomer A as compared to the composition of step (i).

Specifically, the process includes the steps of (a) introducing liquid 1,5,9-cyclododecatriene into a heated vaporization chamber to convert the liquid 1,5,9-cyclododecatriene into a vapor; (b) introducing the vapor from step (a) into a reaction vessel heated to a temperature of from about 400° C. to about 600° C. and at a pressure of from about 0.101 kPa to about 121.5 kPa (1 mbar to 1.2 bar); (c) allowing the 1,5,9-cyclododecatriene of step (b) to thermally rearrange under conditions of temperature, pressure and residence (contact) times to form a 1,2,4-trivinylcyclohexane composition containing low levels of Isomer A; (d) introducing the composition of step (c) into an equilibration vessel; (e) allowing the composition of step (c) to equilibrate in a vapor phase or a liquid phase at a temperature ranging from about 180° C. to about 375° C. and at a pressure ranging from about 0.101 kPa to about 1.013 kPa (1 mbar to 10 bar) to produce a 1,2,4-trivinylcyclohexane composition containing high levels of Isomer A; and (f) removing the equilibrated mixture from step (e) from the equilibration vessel. Optionally, the obtained 1,2,4-trivinylcyclohexane can be further purified by distillation.

The process of the invention can be carried out in a continuous process, in that each step is directly connected to the next step in the process, in a semi-continuous process, in which some portion of the process can be carried out continuously, such as steps (a) to (c), and where the product of step (c) is isolated before the next steps are carried out either in a continuous or batchwise process, or in a batchwise process.

In connection with this process, the vaporizer used in step (a) is a piece of equipment that can heat the liquid phase CDT to convert it into a vapor phase CDT. The vaporizers can be a heated vessel, such as a heated kettle reactor, a heat exchanger, evaporator, or a microwave device, which uses microwaves to convert the liquid to a gas, or other types of vaporizers known in the art.

The reactor used in step (c), i.e., the thermal rearrangement of 1,5,9-cyclododecatriene, can be a hot tube reactor, heat exchanger, evaporator or other reactors which can transfer thermal energy or microwave energy to the gaseous 1,5,9-cyclododecatriene and provide sufficient resonance time for the thermal rearrangement to occur. Preferably, the thermal rearrangement reactor is a hot tube reactor. The reactor may be equipped with a vacuum pump or other device for lower pressure or with a compressor or restrictor if pressures at or above one atmosphere, i.e., 101.3 kPa (1 bar), are desired. The reactor can also be equipped with a source of an inert gas, such as cylinders of nitrogen, argon, or helium, to provide for an inert gas atmosphere to assist in the thermal isomerization of the CDT. The reactor can be made from any material that is suitable for the temperature and pressure requirements of the isomerization, such as metals, metal alloys, glass, or ceramics.

The thermal rearrangement step (c) can be carried out either in the presence or absence of a catalyst. Suitable catalysts are known and have been described for example in U.S. Pat. No. 2,967,895, GB 848637 and SU 390058.

The use of an inert gas, such as argon, helium or nitrogen, can aid in the thermal rearrangement of the CDT. Inert gas partial pressure is equal to or greater than 0.101 kPa (1 mbar), more specifically from about 3 to about 26 kPa (30 mbar to 256 mbar), and most specifically from about 13 kPa to about 15 kPa (128 mbar to 148 mbar) partial pressure.

In one embodiment of the invention, the thermal rearrangement step (c) is carried out at a temperature between 507° C. and 540° C., in the presence of an inert gas with a partial pressure of from about 3 to about 25 kPa, and more specifically between about 13 kPa and about 15 kPa, and a residence time (contact time) of from 6 to 11 seconds.

Advantageously, suitable temperatures for the equilibration step (e) is lower than that needed for the thermal rearrangement of 1,5,9-cyclododecatriene. In one embodiment, the equilibration temperature is from about 180° C. to 375° C., more specifically from about 230° C. to about 350° C., even more specifically from about 230° C. to about 300° C., and most specifically from about 230° C. to about 290° C. Suitable equilibration times are equal to or greater than 1 minute, specifically from about 1 minute to about 15,000 minutes and more specifically, from about 10 minutes to about 3,000 minutes. Suitable pressures are equal to or greater than about 0.101 kPa (1 mbar), specifically from about 0.101 kPa to about 1013 kPa (1 mbar to 10 bars), and more specifically, from 90 kPa to 500 kPa (0.9 bar to 5 bar).

The equilibration can be carried out either in a vapor phase or a liquid phase. As used herein, "vapor phase equilibration" is meant that the composition containing Isomer A and Isomer B is equilibrated in a gaseous state; and "liquid phase equilibration" is meant that the composition containing Isomer A and Isomer B is equilibrated in a liquid state.

There are several ways to carry out vapor phase equilibration. One method is to directly feed the vapor reaction product from step (c) into a hot tube equilibration reactor or equilibration vessel, where the vapor is equilibrated at an equilibration temperature to produce a 1,2,4-trivinylcyclohexane composition containing enriched Isomer A. A second method is to deliver a liquid TVCH composition containing Isomers A and Isomer B, which was prepared in step (c), cooled to a liquid phase and isolated, to a vaporizer. After the liquid composition is converted to a vapor, the vapor is sent to a hot tube equilibration reactor or an equilibration vessel, where the vapor is equilibrated at an equilibration temperature, pressure and equilibration time sufficient to produce a 1,2,4-trivinylcyclohexane composition containing enriched Isomer A. A third method is to purify the mixture of TVCH produced in step (c), collect the purified composition of TVCH as a liquid phase, deliver the purified composition of TVCH liquid to a vaporizer where the liquid is converted into a vapor and the vapor is sent to a hot tube equilibration reactor or equilibration vessel to produce a 1,2,4-trivinylcyclohexane composition containing enriched Isomer A.

Typically, 1,5,9-cyclododecatriene is thermally rearranged in a hot tube reactor. In one embodiment, the vapor exiting the hot tube reactor is first cooled to a suitable equilibration temperature before it is routed to a pipe maintained at the equilibration temperature. In the pipe, the equilibration takes place. The pipe is sized in such a way that it provides the vapor necessary equilibration (residence) time in the range of from about one to about fifteen minutes. The equilibrated product can then be subsequently sent to a downstream CDT/TVCH separation unit, where the desired product is collected. This arrangement is illustrated in FIG. 1.

In case of high TVCH production rates, providing a long pipe sized suitably to provide a residence time of about 1 to about 15 minutes might not be practical. In such cases, an intermediate process vessel maintained at the equilibration temperature could be used. This vessel has to be sized such that the residence time is equal to the desired equilibration time. This arrangement is shown in FIG. 2.

At an alternative to vapor phase equilibration, the equilibration can also be carried out in the liquid phase. Since the boiling point of TVCH is approximately 202° C., conducting equilibration at the desired temperatures in the range of from 230° C. to 350° C. would generate pressures greater than 1 atmosphere. For example, the vapor pressure of TVCH at 300° C. is approximately 709.1 kPa (7 atmospheres). Accordingly, the equipment used for liquid phase equilibration has to be designed to withstand pressure.

Liquid phase equilibration can be carried out in either continuous, semi-continuous, or batch modes. One illustrative continuous mode is shown in FIG. 3. As shown in FIG. 3, in this mode, liquid crude or purified TVCH is pumped to a high-pressure equilibration section, which is essentially an appropriately sized heated and insulated pipe or pressure vessel maintained at the equilibration temperature.

One illustrative batch mode is shown in FIG. 4. As shown in FIG. 4, in this mode, the crude or purified TVCH is pumped periodically from an intermediate storage facility to an equilibration vessel. Once the vessel is full, it is isolated and then heated to the equilibration temperature. After an appropriate equilibration time, the vessel is cooled and the equilibrated TVCH is emptied. This cycle can be repeated continuously.

Alternatively, TVCH containing low levels of Isomer A can be fed to a pressure vessel, which is subsequently heated to the desired equilibration temperature for an appropriate time to provide 1,2,4-trivinylcyclohexane enriched in Isomer A.

It should be understood that the process of the invention does not necessarily require both of steps (i) and (ii) described above (formation of TVC and equilibration). In another embodiment, the present invention is directed to a process of preparing a 1,2,4-trivinylcyclohexane composition enriched in Isomer A which comprises equilibrating a 1,2,4-trivinylcyclohexane composition containing low levels of Isomer A in a vapor phase or a liquid phase at a temperature ranging from about 180° C. to about 375° C. and at a pressure ranging from about 0.101 kPa to about 1.013 kPa to produce a 1,2,4-trivinylcyclohexane composition enriched in Isomer A. This composition can optionally be further purified by distillation.

In this embodiment, the 1,2,4-trivinylcyclohexane composition can be compositions containing 1,2,4-trivinylcyclohexane isomers A and B at a molar ratio of equal to or less than 2.2:1, a purified 1,2,4-trivinylcyclohexane composition in which the byproducts and CDT reactant has been removed using a separation unit, or a crude 1,2,4-trivinylcyclohexane containing unreacted 1,5,9-cyclododecatriene, 1,2,4-trivinylcyclohexane isomers and/or other low molecular weight hydrocarbons. The equilibration can also be performed on 1,2,4-trivinylcyclohexane enriched in the B isomer, which can be obtained by, for example, distillation.

The compositions prepared by the processes of the invention advantageously contain a higher 1,2,4-trivinylcyclohexane Isomer A to trivinylcyclohexane Isomer B ratio as compared to the products prepared by the simple thermal isomerization processes. In one embodiment, the equilibrated product of 1,2,4-trivinylcyclohexane has a molar ratio of Isomer A, the lowest boiling isomer of 1,2,4-trivinylcyclohexane to isomer B, the next higher boiling isomer of 1,2,4-trivinylcyclohexane, of between 2.4:1 and 3.5:1. Optionally, the equilibrated product can be further purified by distillation to further increase the levels of Isomer A.

Accordingly, in another embodiment, there is provided a composition containing 1,2,4-trivinylcyclohexane Isomer A and 1,2,4-trivinylcyclohexane isomer B wherein the molar ratio of isomer A to isomer B is from about 4:1 to 99.9:1, advantageously from 4:1 to 10:1.

The following examples are intended to illustrate, but in no way limit the scope of the present invention. All percentages are by weight based on the total weight of the composition and all temperatures are in degrees Celsius unless explicitly stated otherwise. All patent applications, patents, and other publications cited herein are incorporated by reference in their entireties.

EXAMPLES

Example 1

Preparation of 1,2,4-Trivinylcyclohexane Using the Process, Steps (a) to (c)

CDT was sent to a vaporizer at a preset flow-rate. The vaporizer was a hollow metallic tube that was heated externally by means of an electrical tape. The CDT vapors were then sent to a hot tube reactor, which consisted of a 2" stainless steel (SS316) tube housed in a furnace. The hot tube reactor temperature was varied in the range 450-550° C. The vapors exiting the hot tube reactor were condensed, and the chemical composition of the condensate was analyzed to observe CDT conversion into TVCH, and the A:B ratio. These results are shown in Table 2. Of those results having high selectivity, such results demonstrate a nearly constant A:B ratio in the range of from about 2.0 to about 2.2 irrespective of the hot tube reactor temperature or residence time.

TABLE 2

Data from preparation of 1,2,4-trivinylcyclohexane using process, steps (a) to (c).

| Hot Tube Reactor Temperature, ° C. | Residence Time, seconds | Conversion % | Selectivity % | A:B ratio |
|---|---|---|---|---|
| 458 | 5.13 | 29.3 | 89.4 | 2.18 |
| 465 | 5.15 | 41.4 | 94.1 | 2.17 |
| 467 | 17.20 | 85.4 | 96.3 | 2.13 |
| 473 | 15.10 | 88.6 | 95.0 | 2.19 |
| 474 | 8.09 | 86.6 | 92.1 | 2.13 |
| 475 | 10.10 | 88.2 | 95.9 | 2.12 |
| 477 | 10.00 | 85.6 | 97.7 | 2.14 |
| 478 | 5.00 | 68.8 | 97.5 | 2.12 |
| 478 | 11.60 | 82.9 | 97.3 | 2.13 |
| 480 | 14.80 | 88.9 | 96.5 | 2.20 |
| 482 | 5.03 | 68.9 | 97.9 | 2.15 |
| 486 | 2.09 | 55.7 | 94.8 | 2.08 |
| 486 | 3.06 | 69.2 | 97.8 | 2.09 |
| 486 | 4.98 | 88.3 | 96.2 | 2.03 |
| 487 | 4.96 | 87.2 | 89.6 | 2.06 |
| 488 | 7.40 | 87.9 | 96.6 | 2.13 |
| 489 | 5.26 | 90.4 | 96.1 | 2.06 |
| 489 | 7.45 | 87.3 | 97.3 | 2.12 |
| 493 | 3.04 | 67.9 | 97.5 | 2.13 |
| 495 | 7.01 | 86.9 | 97.9 | 2.16 |
| 498 | 3.12 | 70.8 | 97.3 | 2.15 |
| 498 | 7.10 | 87.7 | 93.4 | 2.16 |
| 498 | 7.49 | 89.2 | 94.9 | 2.20 |
| 499 | 7.50 | 89.4 | 96.0 | 2.21 |
| 502 | 7.01 | 86.9 | 97.6 | 2.17 |
| 510 | 6.88 | 89.1 | 95.4 | 2.17 |
| 515 | 5.25 | 89.4 | 90.8 | 2.15 |
| 521 | 5.08 | 89.5 | 92.2 | 2.17 |
| 522 | 5.21 | 89.8 | 88.6 | 2.16 |
| 523 | 2.95 | 90.8 | 88.7 | 2.07 |
| 527 | 6.95 | 88.5 | 73.3 | 2.19 |
| 527 | 7.36 | 83.6 | 52.4 | 2.48 |
| 528 | 3.05 | 90.9 | 93.2 | 2.07 |
| 533 | 1.96 | 90.6 | 74.1 | 2.03 |
| 540 | 5.13 | 90.7 | 69.5 | 2.14 |
| 549 | 2.76 | 90.1 | 68.6 | 2.06 |

Example 2

Vapor Phase Equilibration

To demonstrate the effect of the equilibration step, a TVCH mixture obtained in accordance with the method of Example 1 was purified via distillation. This purified mixture, with a A:B ratio of approximately 2.2 was sent through the vaporizer into a hot tube reactor maintained at a desired equilibration temperature. After the mixture was equilibrated for a sufficient amount of time, the product was analyzed for A:B ratio. The results and the equilibration conditions are shown in Table 3. Significant increase in the A:B ratio was obtained.

TABLE 3

Data from the vapor phase equilibration.

| Hot Tube Reactor Temperature, ° C. | Residence Time, seconds | A:B ratio | Comments |
|---|---|---|---|
| 280 | 60.2 | 2.55 | |
| 305 | 114.0 | 2.50 | |
| 309 | 445.7 | 2.39 | |
| 345 | 53.7 | 2.35 | slight decomposition of TVCH |

Example 3

Liquid Phase Equilibration

In the vapor phase equilibration experiments conducted in Example 2, a residence time of approximately 1 minute was used. Larger residence times seemed to result in greater TVCH degradation. To counter this, experiments were conducted to study liquid phase equilibration.

TVCH with an A:B ratio of 2.2:1 obtained in accordance with the method of Example 1 was loaded into a Parr reactor that was sealed after loading and heated to the desired equilibration temperature. The reactor contents were maintained at the test temperature for a certain preset time, after which they were cooled to room temperature. Table 4 includes the results of these experiments. Three temperatures, namely 230° C., 270° C., and 300° C. were evaluated. The Experiments illustrated high A:B ratios in the range 2.8:1 to 3.55:1 were obtained when liquid equilibration was used.

Example 4

Effect of Equilibration Time on Isomer A Enrichment

To study the effect of equilibration time on Isomer A enrichment, TVCH with an A:B ratio of 2.2:1 obtained in accordance with the method of Example 1 was loaded into a Parr reactor that was sealed after loading and heated to 230° C. Liquid samples were withdrawn periodically from the Parr reactors and analyzed for molar ratio of Isomer A to Isomer B ratio. The results are shown in FIG. 5. The data demonstrates that the A:B ratio monotonically increases with equilibration time.

Example 5

Effect of Inert Gas on the Products Produced in Step (c) (Thermal Rearrangement)

The reactions were carried out in a manner similar to Example 1, except nitrogen, an inert carrier gas, was added to the hot tube reactor. The results from the thermal conversion of CDT to TVCH are shown in Table 5. The data illustrate that carrying step (i) out at a temperature between about 507° C. to about 540° C. in the presence of an inert gas with a partial pressure of from about 3 to 25 kPa and a residence time of from about 6 seconds to about 11 seconds produces a selectivity of greater than 87.7%.

TABLE 5

The Effect of Inert Gas on Product Composition of Step (c)

| | Example Number | | | | | | | | | | | | | |
|---|---|---|---|---|---|---|---|---|---|---|---|---|---|---|
| | 5A | 5B | 5C | 5D | 5E | 5F | 5G | 5H | 5I | 5J | 5K | 5L | 5M | 5N |
| Pressure, mm Hg | 760 | 760 | 760 | 760 | 753 | 752 | 740 | 754 | 750 | 744 | 740 | 734 | 736 | 200 |
| Temperature, ° C. | 585 | 640 | 540 | 535 | 550 | 500 | 509 | 465 | 513 | 509 | 507 | 474 | 475 | 505 |
| Run time, hours | 1.5 | 0.83 | 1 | 1.67 | 1 | 1 | 1 | 1.17 | 1 | 1 | 1 | 1.17 | 1.33 | 1 |
| Contact time, sec | 4.0 | 4.3 | 6.0 | 11.0 | 7.8 | 8.0 | 8.1 | 9.7 | 8.0 | 8.3 | 7.8 | 9.9 | 11.6 | 2.6 |
| CDT, grams | 48.2 | 48.0 | 44.2 | 44.8 | 44.9 | 46.9 | 44.8 | 46.4 | 45.7 | 44.1 | 47.2 | 43.6 | 41.1 | 44.0 |
| Product mixture, grams | 44.4 | 36.0 | 43.4 | 43.6 | 31.1 | 35.7 | 43.1 | 46.0 | 44.7 | 41.7 | 46.1 | 43.2 | 41.0 | 42.9 |
| TVC, grams | 48.8 | 28.9 | 53.0 | 54.7 | 19.9 | 32.7 | 71.3 | 8.3 | 74.0 | 73.2 | 78.4 | 33.5 | 37.0 | 20.6 |
| Yield[1] (%) | 44.9 | 21.6 | 51.9 | 53.1 | 13.8 | 24.9 | 68.5 | 8.2 | 72.4 | 69.2 | 76.7 | 33.1 | 36.9 | 20.1 |
| Conversion[2] (%) | 61.3 | 92.0 | 54.0 | 56.1 | 98.4 | 97.9 | 87.0 | 9.5 | 74.8 | 78.9 | 79.1 | 34.3 | 37.2 | 22.6 |
| Selectivity[3] (%) | 73.2 | 23.4 | 96.1 | 94.6 | 14.0 | 25.4 | 78.7 | 86.3 | 96.9 | 87.7 | 97.0 | 96.6 | 99.3 | 89.2 |
| $N_2$ flow, mL/min. | 123 | 12 | 17 | 2-19 | 19 | 19 | 19 | 19 | 19 | 19 | 19 | 19 | 19 | 0 |
| $N_2$ volume % in reactant vapor stream[5] | 61 | 8 | 13 | 3-22 | 15 | 14 | 14 | 16 | 14 | 15 | 14 | 17 | 19 | 0 |

[1] Yield = TVC/$CDT_o$
[2] Conversion = ($CDT0 - CDT$)/$CDT_o$
[3] Selectivity = TVC/($CDT_o - CDT$)
[4] CDT = $CDT_o$ (1 − Conversion)
[5] Assumes ideal gas law.

TABLE 4

Data from the liquid phase equilibration.

| Parr reactor Temperature, ° C. | Equilibration Time, min | Pressure (bar-g) | A:B | Comments |
|---|---|---|---|---|
| 300 | 90 | 6 | 3.59 | Viscous due |
| 300 | 20 | 6 | 3.47 | to high residence |
| 300 | 40 | 6 | 3.47 | |
| 300 | 20 | 6 | 3.5 | |
| 300 | 4 | 6 | 3.5 | |
| 270 | 10 | 3 | 3.5 | |
| 230 | 15 | 2 | 2.83 | |

Example 6

Equilibration of 1,2,4-Trivinylcyclohexane Composition Consisting of 10.2 Mole Percent Isomer A and 89.8 Mole Percent Isomer B The effect of equilibration of a distilled 1,2,4-trivinylcyclohexane composition consisting of 10.2 mole percent of Isomer A and 89.8 mole percent of Isomer B at equilibration temperatures ranging from 199° C. to 290° C. was determined. The data are presented in Table 6.

TABLE 6

Data from the equilibration of 1,2,4-trivinylcyclohexane composition consisting of 10.2 mole percent Isomer A and 89.8 mole percent Isomer B.

| Temperature ° C. | Time minutes | TVCH A mole % | TVCH B mole % | TVCH C + D mole % | A/B Ratio |
|---|---|---|---|---|---|
| 199 | 120 | 13.66 | 86.34 | 0.00 | 0.16 |
| 199 | 240 | 27.53 | 72.47 | 0.00 | 0.38 |
| 200 | 60 | 11.56 | 88.44 | 0.00 | 0.13 |
| 200 | 180 | 19.41 | 80.59 | 0.00 | 0.24 |
| 200 | 360 | 34.18 | 65.82 | 0.00 | 0.52 |
| 200 | 2880 | 56.23 | 43.77 | 0.00 | 1.28 |
| 202 | 1440 | 41.63 | 58.37 | 0.00 | 0.71 |
| 227 | 105 | 55.9 | 44.1 | 0.00 | 1.27 |
| 229 | 135 | 60.57 | 39.43 | 0.00 | 1.54 |
| 229 | 195 | 70.31 | 29.69 | 0.00 | 2.37 |
| 230 | 20 | 19.89 | 80.1 | 0.00 | 0.25 |
| 230 | 45 | 31.88 | 68.12 | 0.00 | 0.47 |
| 230 | 225 | 72.72 | 27.28 | 0.00 | 2.67 |
| 230 | 255 | 74.65 | 25.35 | 0.00 | 2.94 |
| 230 | 285 | 75.76 | 24.24 | 0.00 | 3.13 |
| 230 | 305 | 76.62 | 23.38 | 0.00 | 3.28 |
| 253 | 20 | 21.92 | 78.07 | 0.00 | 0.28 |
| 257 | 40 | 42.98 | 57.01 | 0.00 | 0.75 |
| 260 | 60 | 57.08 | 42.92 | 0.00 | 1.33 |
| 260 | 90 | 67.7 | 32.3 | 0.00 | 2.10 |
| 260 | 120 | 71.11 | 28.89 | 0.00 | 2.46 |
| 285 | 10 | 48.62 | 51.38 | 0.00 | 0.95 |
| 289 | 20 | 66.95 | 33.05 | 0.00 | 2.03 |
| 290 | 30 | 72.92 | 27.08 | 0.00 | 2.69 |
| 290 | 45 | 74.38 | 25.62 | 0.00 | 2.90 |
| 290 | 60 | 75.03 | 24.97 | 0.00 | 3.00 |
| 290 | 90 | 74.98 | 25.02 | 0.00 | 3.00 |
| 290 | 120 | 74.92 | 25.08 | 0.00 | 2.99 |

The data indicate that equilibration occurs slowly at the low temperature of 200° C. and has reached an isomer ratio of A:B of only 1.28 after equilibrating the composition for 2,880 minutes. However at higher equilibration temperatures, the equilibration proceeds more quickly to yield isomer ratios greater than 2.2 in shorter reaction times.

Comparative Example A

Equilibration of 1,2,4-Trivinylcyclohexane Composition Consisting of 25 Mole Percent Isomer A and 75 Mole Percent Isomer B The effect of equilibration of a distilled 1,2,4-trivinylcyclohexane composition consisting of 25 mole percent Isomer A and 75 mole percent Isomer B at equilibration temperatures ranging from 450° C. to 510° C. was determined. The data are presented in Table 7.

TABLE 7

Data from the equilibration of 1,2,4-trivinylcyclohexane composition consisting of 25 mole percent Isomer A and 75 mole percent Isomer B.

| Temperature ° C. | Time minutes | TVCH A mole % | TVCH B mole % | TVCH C + D mole % | A/B Ratio |
|---|---|---|---|---|---|
| 450 | 1.042 | 59.61 | 33.28 | 7.11 | 1.79 |
| 450 | 0.677 | 61.59 | 31.08 | 7.33 | 1.98 |
| 450 | 0.399 | 63.01 | 28.06 | 8.94 | 2.25 |
| 450 | 0.258 | 62.40 | 27.53 | 10.07 | 2.27 |
| 450 | 0.204 | 62.58 | 27.37 | 10.05 | 2.29 |
| 450 | 0.152 | 61.74 | 26.94 | 11.32 | 2.29 |
| 470 | 2.095 | 61.80 | 29.46 | 8.74 | 2.10 |
| 470 | 1.742 | 61.99 | 28.47 | 9.54 | 2.18 |
| 470 | 1.380 | 60.50 | 27.27 | 12.23 | 2.22 |
| 470 | 1.049 | 57.59 | 25.65 | 16.76 | 2.25 |
| 470 | 0.679 | 59.14 | 26.23 | 14.63 | 2.26 |
| 470 | 0.335 | 54.82 | 24.10 | 21.08 | 2.27 |
| 470 | 0.257 | 56.51 | 24.81 | 18.69 | 2.28 |
| 470 | 0.207 | 55.72 | 24.41 | 19.87 | 2.28 |
| 490 | 2.533 | 59.85 | 28.77 | 11.38 | 2.08 |
| 490 | 2.127 | 59.77 | 28.54 | 11.68 | 2.09 |
| 490 | 1.761 | 58.40 | 27.88 | 13.71 | 2.09 |
| 490 | 1.341 | 55.84 | 26.00 | 18.16 | 2.15 |
| 490 | 1.050 | 53.75 | 24.78 | 21.47 | 2.17 |
| 490 | 0.668 | 51.72 | 23.66 | 24.62 | 2.19 |
| 490 | 0.335 | 49.95 | 22.70 | 27.34 | 2.20 |
| 490 | 0.253 | 51.11 | 23.12 | 25.78 | 2.21 |
| 510 | 2.074 | 57.46 | 28.49 | 14.04 | 2.02 |
| 510 | 1.382 | 56.65 | 27.86 | 15.49 | 2.03 |
| 510 | 1.035 | 55.70 | 27.23 | 17.07 | 2.05 |
| 510 | 0.699 | 54.16 | 26.28 | 19.56 | 2.06 |
| 510 | 0.344 | 50.91 | 24.13 | 24.95 | 2.11 |
| 510 | 0.258 | 49.36 | 23.02 | 27.62 | 2.14 |

The data indicate that the equilibration can convert Isomer A to Isomer B with formation of Isomer C and/or Isomer D. However, the molar ratio of Isomer A to Isomer B ranges from 1.79:1 to 2.29:1, thereby not producing a 1,2,4-trivinylcyclohexane composition with an isomer ratio of A:B greater than 2.4.

Example 7

Hydrosilation of TVCH

Two different samples of TVCH were hydrosilated using Karsted's platinum catalyst and the same batch of triethoxysilane. Both reactions were run using the same methodology.

In this methodology, TVCH (100 grams) was charged into a 500-mL reaction flask along with catalyst, followed by the dropwise addition of triethoxysilane (81 grams) to the reaction flask using an addition funnel. The catalyst loading was 10 ppm Pt, based on the total charge of triethoxysilane. The reaction was carried out at 106° C. under an atmosphere of dry nitrogen. The same molar quantities of starting materials were used for both reactions.

The first reaction used TVCH with an A/B isomer ratio of 3.77/1. The second reaction used TVCH with an A/B isomer ratio of 1.99/1. In both experiments after all of the triethoxysilane had been added to the reaction pot, the pot contents were monitored over time by GC analysis for the amount of silylated TVCH present and for the disappearance of triethoxysilane.

The data showed that both reactions contained similar concentrations of silylated TVCH and triethoxysilane after all the triethoxysilane had been charged. The data also show that significant quantities of unreacted starting materials remained at the end of the triethoxysilane addition.

Figure 6:
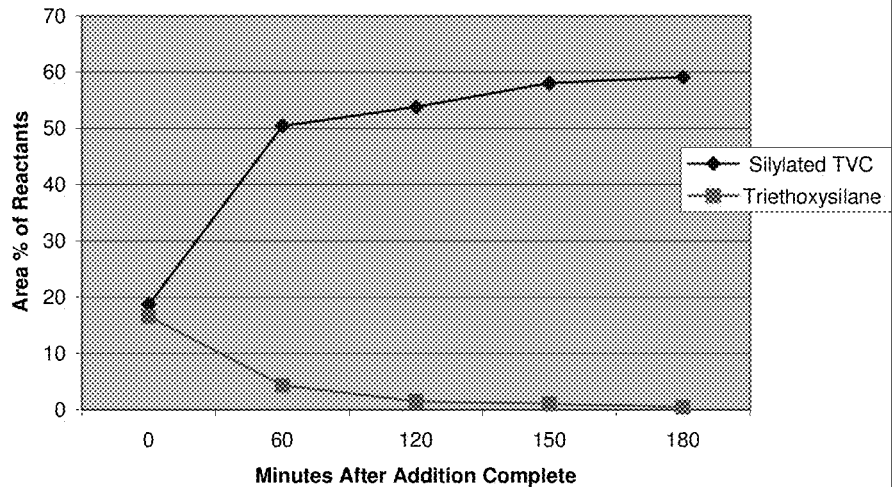
FIG. 6 illustrates the progress of hydrosilation of TVCH with Isomer A/B ratio of 3.77:1.
Figure 7:
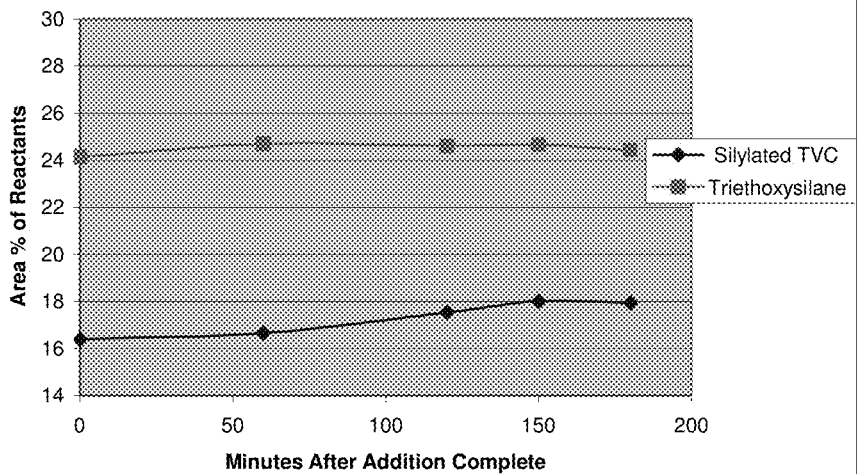
FIG. 7 illustrates the progress of hydrosilation of TVCH with Isomer A/B ratio of 1.99:1.

Additional time was then given to allow the reaction to reach completion. The progress of both reactions from this point forward is shown in FIGS. 6 and 7. These figures illustrate that only the TVCH with the high isomer A/B ratio continued to undergo hydrosilylation, until the reaction reached completion in about 3 hours. The TVCH with the lower Isomer A content (A/B of 1.99) showed essentially no additional consumption of triethoxysilane, indicating that the reaction had terminated without reaching completion.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A process for preparing a 1,2,4-trivinylcyclohexane composition enriched in Isomer A—1,trans-2,trans-4-trivinyl-cyclohexane, the lowest boiling geometric isomer of 1,2,3-trivinylcyclohexane—having the three-dimensional structure of

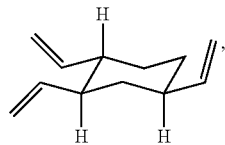

comprising:
(i) heating 1,5,9-cyclododecatriene at a temperature of from about 400° C. to about 600° C. and at a pressure of from about 1 mbar to about 1.2 bar thereby forming a 1,2,4-trivinylcyclohexane composition containing low levels of Isomer A; and
(ii) subsequently equilibrating the composition from step (i) in a vapor phase or a liquid phase at a temperature ranging from about 180° C. to about 375° C. and at a pressure ranging from about 1 mbar to about 10 bar to produce a 1,2,4-trivinylcyclohexane composition enriched in Isomer A as compared to the composition of step (i).

2. The process of claim 1 wherein the 1,2,4-trivinylcyclohexane composition of step (ii) has a molar ratio of Isomer A, the lowest boiling isomer of 1,2,4-trivinylcyclohexane to isomer B, 1,trans-2,cis-4-trivinyl-cyclohexane having the three-dimensional structure of

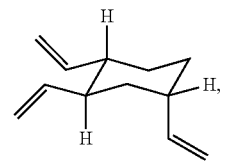

the next higher boiling isomer of 1,2,4-trivinylcyclohexane, of between 2.4:1 and 3.5:1.

3. The process of claim 1 wherein step (i) is carried out at a temperature between about 507° C. and about 540° C., in the presence of an inert gas with a partial pressure of from about 30 mbar to about 256 mbar and a residence time of from about 6 seconds to about 11 seconds.

4. The process of claim 3 wherein step (i) is carried out in the presence of an inert gas at a partial pressure of from about 128 mbar to about 148 mbar.

5. The process of claim 1 wherein step (ii) is carried out at a temperature of from about 230° C. to about 350° C.

6. The process of claim 4 wherein step (ii) is carried out at a temperature of from about 230° C. to about 290° C.

7. The process of claim 1 wherein the composition of step (i) is equilibrated in a liquid phase.

8. The process of claim 1 wherein the composition of step (i) is equilibrated in a vapor phase.

9. The process of claim 7 wherein the composition of step (i) is equilibrated at a pressure of from 1 bar to 10 bar.

10. The process of claim 1 wherein the process for preparing 1,2,4-trivinylcyclohexane compositions enriched in Isomer A is carried out in a continuous, a semi-continuous, or a batch process.

11. The process of claim 10, wherein the process for preparing 1,2,4-trivinylcyclohexane compositions enriched in Isomer A is carried out in a continuous process.

12. The process of claim 11, wherein the process for preparing 1,2,4-trivinylcyclohexane compositions enriched in Isomer A is carried out in a semi-continuous process.

13. The process of claim 1, wherein step (i) is carried out without the presence of any catalyst.

14. The process of claim 1, wherein step (i) is carried out in the presence of a catalyst.

15. The process of claim 1, wherein the composition of step (ii) is purified by distillation to provide a purified 1,2,4-trivinylcyclohexane composition.

16. The process of claim 15, wherein the purified 1,2,4-trivinylcyclohexane composition has a molar ratio of Isomer A to Isomer B of from 4.0:1 to 99.9:1.

17. A process for preparing 1,2,4-trivinylcyclohexane compositions enriched in Isomer A, 1,trans-2,trans-4-trivinyl-cyclohexane having the three-dimensional structure of

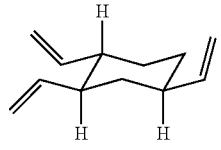

comprising: equilibrating a 1,2,4-trivinylcyclohexane composition containing low levels of Isomer A in a vapor phase or a liquid phase at a temperature ranging from about 180° C. to about 375° C. and at a pressure ranging from about 1 mbar to about 10 bar to produce a 1,2,4-trivinylcyclohexane composition enriched in Isomer A.

18. The process of claim 17, wherein the 1,2,4-trivinylcyclohexane composition having a molar ratio of Isomer A to Isomer B of less than 2.2 is equilibrated at a temperature of from 230° C. to 290° C. and at a pressure of from 1 bar to 10 bar.

19. The process of claim 17 wherein the equilibration is carried out for about one minute to about fifteen thousand minutes.

20. A composition containing 1,2,4-trivinylcyclohexane Isomer A and 1,2,4-trivinylcyclohexane isomer B wherein the molar ratio of isomer A to isomer B is from about 4:1 to 99.9:1.

21. The composition of claim 20 wherein the molar ratio of isomer A to isomer B is from about 4:1 to 10:1.

* * * * *